United States Patent
Shuber et al.

(10) Patent No.: US 10,947,599 B2
(45) Date of Patent: Mar. 16, 2021

(54) TUMOR MUTATION BURDEN

(71) Applicant: GENETICS RESEARCH, LLC, Wakefield, MA (US)

(72) Inventors: Anthony P. Shuber, Wakefield, MA (US); William Glover, Wakefield, MA (US)

(73) Assignee: GENETICS RESEARCH, LLC, Worcester, MA (US)

( * ) Notice: Subject to any disclaimer, the term of this patent is extended or adjusted under 35 U.S.C. 154(b) by 183 days.

(21) Appl. No.: 15/877,618

(22) Filed: Jan. 23, 2018

(65) Prior Publication Data
US 2018/0355436 A1    Dec. 13, 2018

Related U.S. Application Data

(60) Provisional application No. 62/568,114, filed on Oct. 4, 2017, provisional application No. 62/526,091, filed on Jun. 28, 2017, provisional application No. 62/519,051, filed on Jun. 13, 2017.

(51) Int. Cl.
| | |
|---|---|
| *C12Q 1/6886* | (2018.01) |
| *C12Q 1/6827* | (2018.01) |
| *G16H 50/20* | (2018.01) |
| *G16H 50/50* | (2018.01) |
| *G16H 50/70* | (2018.01) |
| *G16H 50/30* | (2018.01) |
| *G16H 10/40* | (2018.01) |
| *C12Q 1/6806* | (2018.01) |

(52) U.S. Cl.
CPC ......... *C12Q 1/6886* (2013.01); *C12Q 1/6806* (2013.01); *C12Q 1/6827* (2013.01); *G16H 10/40* (2018.01); *G16H 50/20* (2018.01); *G16H 50/30* (2018.01); *G16H 50/50* (2018.01); *G16H 50/70* (2018.01); *C12Q 2600/118* (2013.01); *C12Q 2600/156* (2013.01); *C12Q 2600/158* (2013.01); *C12Q 2600/166* (2013.01); *G01N 2800/50* (2013.01); *G01N 2800/52* (2013.01); *G01N 2800/54* (2013.01); *G01N 2800/56* (2013.01); *G01N 2800/60* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 6,297,010 | B1 | 10/2001 | Stefano |
| 8,318,445 | B2 | 11/2012 | Bernard et al. |
| 10,011,849 | B1 | 7/2018 | Gill et al. |
| 10,081,829 | B1 | 9/2018 | Shuber et al. |
| 2003/0215854 | A1 | 11/2003 | Clausen et al. |
| 2004/0197804 | A1 | 10/2004 | Keefe et al. |
| 2006/0183109 | A1 | 8/2006 | Dahlberg et al. |
| 2008/0254516 | A1 | 10/2008 | St. John et al. |
| 2009/0053715 | A1 | 2/2009 | Dahlhauser |
| 2012/0315633 | A1 | 12/2012 | Mantzaris et al. |
| 2013/0059762 | A1 | 3/2013 | Leamon et al. |
| 2014/0356867 | A1 | 12/2014 | Peter et al. |
| 2015/0105284 | A1 | 4/2015 | Willson et al. |
| 2015/0211058 | A1 | 7/2015 | Carstens |
| 2015/0292033 | A1 | 10/2015 | Wang et al. |
| 2016/0002720 | A1 | 1/2016 | Richard |
| 2016/0017396 | A1 | 1/2016 | Cann et al. |
| 2016/0130664 | A1 | 5/2016 | Albitar |
| 2016/0153005 | A1 | 6/2016 | Zhang et al. |
| 2016/0319262 | A1 | 11/2016 | Doudna et al. |
| 2017/0022551 | A1 | 1/2017 | Liu et al. |
| 2017/0044592 | A1 | 2/2017 | Peter et al. |
| 2017/0053062 | A1 | 2/2017 | Cradick et al. |
| 2017/0114413 | A1 | 4/2017 | Hahn et al. |

FOREIGN PATENT DOCUMENTS

| | | |
|---|---|---|
| EP | 3150718 A1 | 4/2017 |
| WO | 1995/006752 A1 | 3/1995 |
| WO | 99/39003 A1 | 8/1999 |
| WO | 2000/011222 A1 | 3/2000 |
| WO | 2003/027258 A2 | 4/2003 |
| WO | 2008/104794 A2 | 9/2008 |
| WO | 2010/014920 A1 | 2/2010 |
| WO | 2015/075056 A1 | 5/2015 |
| WO | 2016/014409 A1 | 1/2016 |
| WO | 2016/028843 A2 | 2/2016 |
| WO | 2016/028887 A1 | 2/2016 |

(Continued)

OTHER PUBLICATIONS

Campesato, 2015, Comprehensive cancer-gene panels can be used to estimate mutational load and predict clinical benefit to PD-1 blockade in clinical practice, Oncotarget 6(33):34221-34227.

Chalmers, 2017, Analysis of 100,000 human cancer genomes reveals the landscape of tumor mutational burden, Genome Med 9(34):1-14.

Chen, 2018, CRISPR-Cas12a target binding unleashes indiscriminate single-stranded DNase activity, Science aar6245 (8 pages).

(Continued)

*Primary Examiner* — Antonio Galisteo Gonzalez
(74) *Attorney, Agent, or Firm* — Brown Rudnick LLP; Thomas C. Meyers (57) ABSTRACT

The invention provides methods for determining the mutation burden of a tumor by assaying tumor DNA that is representative of genetic loci that are themselves representative of genetics of the tumor. The assayed tumor DNA may be itself agnostic as to loci, so long as it is representative of loci that are representative of tumor mutation burden. The invention provides for assays in which the tumor DNA being sequenced or tested can be something other than, and possibly less than, a full panel of oncogenes that is expected to stand for a tumor's mutational load.

13 Claims, 7 Drawing Sheets

(56) References Cited

FOREIGN PATENT DOCUMENTS

| | | | |
|---|---|---|---|
| WO | 2016/094867 A1 | 6/2016 |
| WO | 2016/100955 A2 | 6/2016 |
| WO | 2016/100974 A1 | 6/2016 |
| WO | 2016/134136 A2 | 8/2016 |
| WO | 2016/144810 A1 | 9/2016 |
| WO | 2016/172727 A1 | 10/2016 |
| WO | 2017/031360 A1 | 2/2017 |
| WO | 2017/053762 A1 | 3/2017 |
| WO | 2017/218512 A1 | 12/2017 |
| WO | 2018/068028 A1 | 4/2018 |

OTHER PUBLICATIONS

Fu, 2013, High frequency off-target mutagenesis induced by CRISPR-Cas nucleases in human cells, Nat Biotech 31(9)822-826.
Gootenberg, 2018, Multiplexed and portable nucleic acid detection platform with Cas13, Cas12a, and Csm6, Science aaq0179 (10 pages).
Hahn, 2009, Microsystem for isolation of fetal DNA from maternal plasma by preparative size separation, Clin Chem 55(12)2144-2152.
Hsieh, 2010, Electrochemical DNA detection via exonuclease and target-catalyzed transformation of surface-bound probes, Langmuir 26(12)10392-10396.
Hsu, 2013, DNA targeting specificity of RNA-guided Cas9 nucleases, Nat Biotech 31(9):827-832.
International Search Report and written Opinion dated Aug. 27, 2018, for PCT/US2018/037294, filed Jun. 13, 2018 (10 pages).
International Search Report and written Opinion dated Aug. 27, 2018, for PCT/US2018/037312, filed Jun. 13, 2018 (10 pages).
International Search Report and written Opinion dated Aug. 28, 2018, for PCT/US2018/037273, filed Jun. 13, 2018 (10 pages).
International Search Report and written Opinion dated Aug. 29, 2018, for PCT/US2018/037287, filed Jun. 13, 2018 (10 pages).
International Search Report and written Opinion dated Sep. 11, 2018, for PCT/US2018/037310, filed Jun. 13, 2018 (8 pages).
International Search Report and written Opinion dated Sep. 12, 2018, for PCT/US2018/037307, filed Jun. 13, 2018 (8 pages).
International Search Report and written Opinion dated Sep. 13, 2018, for PCT/US2018/037296, filed Jun. 13, 2018 (11 pages).
International Search Report and written Opinion dated Sep. 17, 2018, for PCT/US2018/037277, filed Jun. 13, 2018 (9 pages).
International Search Report and written Opinion dated Sep. 21, 2018, for PCT/US2018/039518, filed Jun. 26, 2018 (8 pages).
International Search Report and written Opinion dated Sep. 26, 2018, for PCT/US2018/037280, filed Jun. 13, 2018 (18 pages).
Larsson, 2004, In situ genotyping individual DNA molecules by target-primed rolling-circle amplification of padlock probes, Nat Meth 1(3):227-232.
Lee, 2017, CUT-PCR: CRISPR-mediated ultrasensitive detection of target DNA using PCR, Ocogene 36 (49):6823-6829.
Lescarbeau, 2017, A reanalysis of Schaefer et al does not indicate extensive CRISPR/Cas9 mediated off-target editing events, bioRxiv.
Leung, 2012, Luminescent detection of DNA-binding proteins, Nucleic Acids Res 40(3):941-55.
Pattanayak, 2013, High-throughput profiling of off-target DNA cleavage reveals RNA-programmed Cas9 nuclease specificity, Nat Biotech 31(9)839-843.
Schaefer, 2017, Unexpected mutations after CRISPR-Cas9 editing in vivo, Nat Meth 14(6):547-550.
Tosi, 2017, Long-adapter single-strand oligonucleotide probes for the massively multiplexed cloning of kilobase genome regions, Nat Biomed Eng 1:92.
Wang, 2014, Genetic screens in human cells using the CRISPR/Cas9 system, Science 343(6166):80-84.
Wang, 2018, CRISPR-typing PCR (ctPCR), a new Cas9-based DNA detection method, Sci Rep 8(1):14126.
Xu, 2015, An improved protocol for small RNA library construction using high definition adapters, Meth Next-Gen Seq 2:1-10.
Zehir, 2017, Mutational landscape of metastatic cancer revealed from prospective clinical sequencing of 10,000 patients, Nat Med 23(6):703-713.
Zhang, 2015, Use of genome-wide association studies for cancer research and drug repositioning, PLoS One 10(3): e0116477.
Zhang, 2018, Detection of target DNA with a novel Cas9/sgRNAs-associated reverse PCR (CARP) technique, Anal Bioanal Chem 410(12):2889-2900.
Zischewski, 2017, Detection of on-target and off-target mutations generated by CRISPR/Cas9 and other sequence-specific nucleases, Biotech Adv 35(1):95-104.
Altmuller, 2014, Enrichment of target sequence for next-generation sequencing applications in research and diagnostics, Biol Chem 395(2):231-37.
Deleavey, 2012, Designing chemically modified oligonucleotides for targeted gene silencing, Chem Biol 19(8):937-54.
Harrington, 2017, A thermostable Cas9 with increased lifetime in human plasma, Nat Commun 8(1):1424.
Jiang, 2015, Cas9-assisted targeting of chromosome segments catch enables one-step targeted cloning of large gene clusters.
Jinek, 2012, A programmable dual-RNA-guided DNA endonuclease in adaptive bacterial immunity, Science 337 (6096):816-821.
Kozarewa, 2015, Overview of Target Enrichment Strategies, Curr Protoc Mol Biol 112(7):1-23.
Mertes, 2011, Targeted enrichment of genomic DNA regions for next-generation sequencing, Brief Funct Genomics 10(6):374-86.
Monia, 1996, Nuclease resistance and antisense activity of modified oligonucleotides targeted to Ha-ras, J Biol Chem 271(24):14533-40.
Zetsche, 2015, Cpf1 is a single RNA-guided endonuclease of a class 2 CRISPR-Cas system, Cell 163(2):759-71.
Zischewski, 2017, Detection of on-target and off-target mutations generated by CRISPR/Cas9 and other sequence-specific nucleases, Biotechnology Advances 65:95-104.

TUMOR MUTATION BURDEN

CROSS-REFERENCE TO RELATED APPLICATIONS

This application claims the benefit of, and priority to, U.S. Provisional Application No. 62/568,114, filed Oct. 4, 2017, U.S. Provisional Application No. 62/526,091, filed Jun. 28, 2017, and U.S. Provisional Application No. 62/519,051, filed Jun. 13, 2017, the contents of each of which are incorporated by reference.

TECHNICAL FIELD

The disclosure relates to oncogenomics.

BACKGROUND

Immunotherapy is a promising approach to cancer treatment that can potentially treat cancers previously thought to be untreatable. Unfortunately, immunotherapy comes with undesirable side-effects and a large number of patients do not even respond to immunotherapy.

It has been proposed that tumor molecular profiling to determine the mutational landscape of a tumor may be predictive for response to immunotherapy. Studying the mutational landscape of tumors can reveal, for example, recurrent targetable alterations across distinct tumor types. A tumor's mutational landscape potentially includes protein-coding mutations, copy number alterations, promoter mutations and structural rearrangements in cancer-associated genes. One way to characterize a tumor's mutational landscape is to look at tumor mutational burden (TMB).

TMB is a measure of the number of mutations within a tumor genome and is one measure of a mutational landscape of a tumor. Tumors with a greater number of mutations are thought to potentially have a greater likelihood of response to immunotherapy. It has been hypothesized that the mutation burden correlates to a number of mutated proteins in a tumor cell, such that a high TMB indicates a high number of mutated proteins, or neo-antigens. Those neo-antigens can elicit an immune response and thus represent an immune potential that contributes to the effectiveness of immunotherapy.

Evidence suggests that TMB measured using whole exome sequencing may be predictive of immunotherapy response. Some have sought to measure TMB by massively parallel sequencing of certain panels of oncogenes. However, sequencing a full panel of oncogenes or an entire exome requires materials and reagents to consistently capture the full panel of targets. Moreover measuring TMB by sequencing a panel of oncogenes takes for granted that the panel is a reliable proxy for TMB in every patient, for every tumor type, under all conditions.

SUMMARY

The invention provides methods for determining the mutational landscape of a tumor by obtaining a representative sample that contains tumor DNA and sequencing a representative portion of the tumor DNA. The sequenced portion of the tumor DNA may be agnostic as to loci, so long as it is representative of a mutational landscape of the tumor. For example, the sequenced portion may be one long fragment of tumor DNA for which is has been, or can be, demonstrated that mutations in the portion reliably correlate to mutations in the tumor. The invention provides for assays in which the tumor DNA being sequenced or tested can be something other than, and possibly less than, a full panel of oncogenes that is expected to stand for a tumor's mutational load. Using the representative portion of tumor DNA to characterize the tumor's mutational landscape is valuable in the context of immunotherapy. By examining mutations in the representative portion of tumor DNA, immunotherapy choices can be driven, allowing clinicians to select and recommend effective immunotherapies.

Mutational landscape of a tumor may include clinically relevant somatic mutations, novel noncoding alterations, and mutational signatures that are shared by common and rare tumor types. In certain preferred embodiments, methods of the invention are used to determine a mutational landscape by reporting TMB for a tumor. Mutational landscape generally includes deviations from a normal tissue genome or reference genome. Different types of deviations from the normal tissue genome or reference genome can be scored or evaluated differently, with a different score for SNPs, indels, rearrangements, CNVs, etc. Moreover, mutations that are known to have different impacts on the relevance of immunotherapy can have different implications for calculating a mutational score. Methods include evaluating a mutational landscape of a tumor by sequencing a representative portion of tumor DNA.

The portion of tumor DNA to be sequenced may be demonstrated to be representative of mutations in the tumor, and the starting sample (such as tissue from a biopsy) maybe demonstrated to represent a population of cells in the tumor. Through those demonstrable relationships, sequences from the representative portion of the tumor DNA can be analyzed to characterize mutational landscape. For example, a count of mutations in the representative portion of tumor DNA can be correlated to a measure of TMB for the tumor. That the sequenced portion of tumor DNA is representative of mutations in the tumor can be demonstrated using suitable methods such as statistical, biochemical, or genetic methods. This allows the tumor DNA to be obtained by techniques that are un-coupled from any requirement of targeting any specific loci. Thus, tumor DNA may be obtained using techniques such as random fragmentation, polynucleotide enrichment using DNA binding proteins, size fractionation, or other techniques.

The sample itself can be demonstrated to be representative of a population of cells in the tumor, or the tumor DNA sample may be obtained using methods and kits, that have been demonstrated to yield a representative sample. A sample may be shown to be a representative sample by any suitable methods. For example, the sampling method may be tested against an empirical standard; a technique such as a Bayesian regression, bootstrap re-sampling, or a Monte Carlo Markov chain analysis may show that the sample is a representative sample; genetic analyses such as linkage disequilibrium or genome-wide association studies may be employed. Different loci and/or different scoring algorithms may be used for different cancers. For example, loci such as PD-L1, the mismatch repair pathway (MMR), BRCA1, or known trans-membrane proteins, may be included to aid in the selection of immunotherapy for various cancer types.

In one illustrative embodiment, a portion of a tumor DNA sample is obtained using a polynucleotide enrichment process in which the representative portion is protected using a binder such as a Cas endonuclease and guide RNA while un-protected, non-target nucleic acid is digested promiscuously. In parallel, another sample from the same tumor is subject to whole-exome sequencing or comprehensive genomic profiling by next-generation sequencing (NGS) to determine TMB. The enriched portion of tumor DNA is assayed for mutations and a count of mutations is correlated to the NGS-determined TMB. Conditions of the enrichment are varied (e.g., different guide RNAs may be used) and for each set of conditions, multiple replicates of enrichment and assay are performed until the enrichment and assay stably provides a mutation count that reliably correlates to NGS-determined TMB. The enrichment conditions yielding such result are thus shown to provide a representative sample. When such methods are employed with, for example, a given patient, the same sample enrichment may then be used during future patient visits for benefits such as monitoring treatment progress or remission.

An important benefit of the disclosed enrichment process is the avoidance of problems such as GC bias with PCR. Another important benefit is that the enrichment process provide representative portions of tumor DNA for sequencing, in which those portions include fragments that can be significantly longer, and arbitrarily longer, than what can be provided by PCR.

In certain aspects, the invention provides a method of analyzing a tumor. The method includes obtaining a representative sample of a tumor. The sample includes tumor DNA. The method includes sequencing a portion of the tumor DNA representative of mutations in the tumor to identify mutations and reporting a tumor mutation burden (TMB) based on the identified mutations. The representative sample may include tissue obtained by tumor biopsy. The method preferably includes isolating the representative portion of the tumor DNA from the representative sample without targeting known, specified tumor biomarkers.

In some embodiments, the representative portion comprises one or more DNA fragments at least a few kilobases in length. For example, the representative portion may be a long fragment (e.g., >8,000 bases) that includes portions of both genes and non-coding DNA, any or all of which may be sequenced.

Optionally, an enrichment is performed to obtain the representative portion from the tumor DNA. The enrichment may include selectively protecting the representative portion and degrading unprotected nucleic acid. Selectively protecting the representative portion may include introducing into the sample at least one molecule that selectively protects the representative portion from digestion in a sequence-specific manner (e.g., the at least one molecule is a guide RNA where selectively protecting the representative portion includes delivering the guide RNA and a Cas endonuclease to bind to, and protect, the representative portion in the sequence-specific manner, and degrading the unprotected nucleic acids includes digesting the unprotected nucleic acids with an exonuclease).

Optionally the representative portion does not include any portion of any oncogene. Embodiments of the method may include demonstrating that the representative portion is representative of the tumor DNA. In some embodiments, the demonstrating includes a Bayesian regression or a genome-wide association study. The method may include showing that the TMB predictably correlates with the identified mutations, thereby showing that the representative portion is representative of mutations in the tumor and that the representative In some embodiments, identifying the mutations includes determining differences between the portion of the tumor DNA and matched normal DNA. Determining differences between the portion of the tumor DNA and the matched normal DNA may include sequencing the portion of the tumor DNA and the matched normal DNA to produce tumor sequences and normal sequences and aligning the tumor sequences to the normal sequences. The method may further include aligning the tumor sequences or the normal sequences to a reference genome. Preferably, the determined differences include bases and small indels in the tumor DNA that are unmatched at homologous portions of the normal DNA and the reference genome.

The representative portion may include genes or sequences that are not elsewhere included in TMB panels. For example, the representative portion of tumor DNA may include one or more housekeeping genes. The representative portion of tumor DNA may include fewer than one million bases of DNA. In some embodiments, the representative sample comprises plasma comprising cell-free DNA from the patient, and the tumor DNA is circulating tumor DNA from the sample. In preferred embodiments, the representative sample is tissue from a tumor.

The method may include obtaining the representative portion of the tumor DNA from the sample by a negative enrichment, e.g., selectively protecting at least one fragment of the tumor DNA in a sequence-specific manner with a binding molecule such as a Cas endonuclease and a guide RNA and degrading unprotected nucleic acid, thereby isolating the representative portion of the tumor DNA, wherein the at least one fragment is at least five thousand bases in length.

Aspects provide a method that includes obtaining a portion of tumor DNA demonstrably representative of a mutational landscape of the tumor, and a sample demonstrably representative of a population of cells in the tumor.

In some aspects, the invention provides a method of analyzing a tumor that includes obtaining tumor DNA from a tumor of patient, in which the obtained tumor DNA does not include a plurality of known oncogenes. A number of mutations in a representative portion of th tumor DNA is identified and the method includes determining, from the number of mutations, a mutational landscape for the tumor based on a relationship by which the portion of the tumor DNA is representative of the tumor mutational landscape.

In certain aspects, the invention provides methods for analyzing a tumor. The method may include obtaining a sample comprising tumor DNA from a tumor in a patient. The sample is representative of a plurality of genetic loci, where mutations at the plurality of genetic loci are representative of a total number of mutations in the tumor. The method includes determining differences between the tumor DNA and matched normal DNA and reporting tumor mutation burden (TMB) based on the determined differences.

In some embodiments, obtaining the sample includes obtaining a blood, plasma, or tissue sample from the patient; selectively protecting at least one fragment of the tumor DNA; and degrading unprotected, non-target nucleic acids, thereby isolating the tumor DNA. Preferably, the at least one fragment of the tumor DNA is at least a few kilobases in length. Selectively protecting the at least one fragment may be done by introducing into the sample at least one molecule (e.g., a guide RNA along with a Cas endonuclease) that selectively protects the target nucleic acid from digestion in a sequence-specific manner. Selectively protecting the target nucleic acid may be done by delivering the guide RNA and a Cas endonuclease to bind to, and protect, the target nucleic acid in the sequence-specific manner while degrading the non-target nucleic acids may be done by digesting the non-target nucleic acids with an exonuclease.

The method may include demonstrating that the sample is representative of the plurality of genetic loci. The demonstrating may include a genome-wide association study.

In certain embodiments, the plurality of genetic loci includes exons of each of a plurality of genes, and the sample does not include any of the exons of the plurality of genes.

The method may include demonstrating that the plurality of genetic loci is representative of a total number of mutations in the tumor. The method may include extrapolating the TMB from a count of the determined differences. The method may include showing that the TMB predictably correlates with the determined differences, thereby showing that the sample is representative of a plurality of genetic loci and that the plurality of genetic loci is representative of a total number of mutations in the tumor. It may be that the sample being representative of a plurality of genetic loci and the plurality of genetic loci being representative of a total number of mutations in the tumor mean that the TMB predictably correlates with the determined differences.

Determining differences between the tumor DNA and the matched normal DNA may be done by sequencing the tumor DNA and the matched normal DNA to produce tumor sequences and normal sequences and aligning the tumor sequences to the normal sequences. The method may include aligning the tumor sequences or the normal sequences to a reference genome. Determine differences may include bases and small indels in the tumor DNA that are unmatched at homologous portions of the normal DNA and the reference genome.

In some embodiments, the tumor DNA comprises one or more housekeeping genes. Optionally, the tumor DNA comprises fewer than one million bases of DNA. In one preferred embodiment, the sample comprises plasma comprising cell-free DNA from the patient, and the tumor DNA is circulating tumor DNA from the sample. In the one preferred embodiment, obtaining the sample includes selectively protecting at least one fragment of the tumor DNA in a sequence-specific manner with a Cas endonuclease and a guide RNA and degrading unprotected, non-target nucleic acids, thereby isolating the tumor DNA. The at least one fragment may preferably be at least five thousand bases in length.

Aspects of the invention provide a method that includes obtaining a sample demonstrably representative of a fraction of tumor nucleic acid that is demonstrably representative of genotype of a tumor.

In other aspects, the invention provides a method of analyzing a tumor. The method includes obtaining tumor DNA from a tumor of patient, in which the obtained tumor DNA does not include a plurality of known oncogenes. The method includes identifying a number of mutations in the tumor DNA and determining—from the number of mutations—tumor mutation burden for the tumor based on a relationship by which the tumor DNA is representative of a genome of the tumor.

DETAILED DESCRIPTION

The invention uses a representative sample for the determination of a mutational landscape of a tumor. Methods include identifying mutations in a representative portion of tumor DNA from the sample. Any suitable representative portion may be used. For example, the representative portion may be an entire exome or a comprehensive genomic profile of a panel of genes. However, in most preferred embodiments, the representative portion is not a panel or exome, but may be something less (e.g., fewer bases of tumor DNA than an entire exome or panel). The representative portion may have a demonstrated statistical likelihood to correlate predictably with nucleic acid such that a count of mutations in the sample can be extrapolated to show the mutational landscape.

In most preferred embodiments, the representative portion includes tumor DNA and, preferably, far fewer than one million bases of DNA from a tumor. In certain embodiments, the representative portion includes only coding regions of a portion of a genome. In some embodiments, the representative portion includes one or a combination of housekeeping genes such as genes for transcription factors, RNA splicing proteins, translation factors, ribosomal proteins, mitochondrial ribosomal proteins, RNA polymerase, heat shock proteins, histones, cell-cycle proteins, apoptosis genes, oncogenes, DNA repair and replication genes, metabolic genes, NADH dehydrogenase, cytochrome c oxidase, ATPase, lysosome, proteasome, ribonuclease, cytoskeletal genes, cell adhesion proteins, or other such genes. It may be found that such genes or a subset thereof are useful as a representative sample.

By selecting a representative sample that includes tumor DNA and a representative portion of that tumor DNA, the ability to determine TMB is improved. For example, a sample can be selected for its ease of sequencing. Due to non-uniform sequence coverage in NGS instruments, whole exome sequencing may include a very large amount of redundant and essentially uninformative sequence. That can be avoided by isolating a sample that is demonstrably representative of the tumor and isolating a representative portion of tumor DNA form the sample, and sequencing the representative portion.

Embodiments of the invention include techniques for isolating fragments of tumor (and matched normal) DNA while degrading off-target DNA, thereby enriching for those fragments. Where such techniques are employed, methods can be used to show that the fragments are representative, and those fragments can be sequenced to determine TMB. Sequencing a small number of isolated fragments can proceed quickly and efficiently by avoiding the excessive redundancy inherent to whole exome sequencing by NGS.

Figure 1:
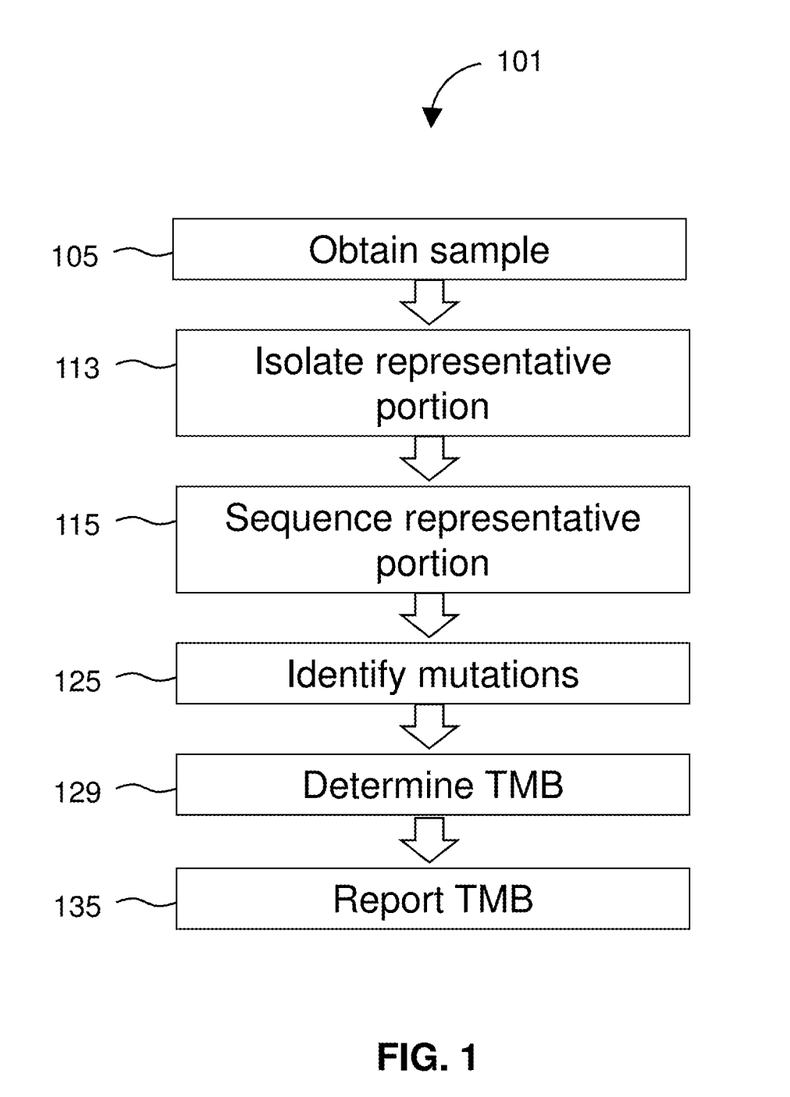
FIG. 1 diagrams a method for analyzing a tumor.

FIG. 1 shows a method 101 of analyzing a tumor. The method includes obtaining 105 a representative sample of a tumor. The sample includes tumor DNA. The method includes sequencing 115 a portion of the tumor DNA representative of mutations in the tumor to identify 125 mutations and determining 129 a tumor mutation burden (TMB) based on the identified mutations. Preferably, the method 101 includes providing 135 a report of the TMB for the tumor. The method preferably includes isolating 113 the representative portion of the tumor DNA from the representative sample without targeting known, specified tumor biomarkers.

Methods of the invention use a representative portion of tumor DNA from a representative sample for a tumor for the determination of TMB. Existing paradigms use whole exome sequencing for comprehensive genomic profiling, by NGS, of panels of dozens of genes. That whole exome, or a panel of dozens of genes, may not be representative of TMB. For example, a tumor may include genetic heterogeneity in the form of a diverse genotypes among tumor cells. Simply capturing one panel of genes and sequencing those may miss important driver mutations even when the relevant locus is within the sequenced sample. Here, what is done is to show that a given sample represents the relevant loci and also represents tumor heterogeneity.

Embodiments of the invention may use a two-part process. In one part, a representative portion of tumor DNA is demonstrated to be representative of tumor mutations. In another part, such a sample is assayed for a number of mutations and TMB is reported based on the assayed number of mutations. Methods of the invention may employ polynucleotide enrichment techniques with particular applicability for long-fragment capture for long-read sequencing.

Figure 2:
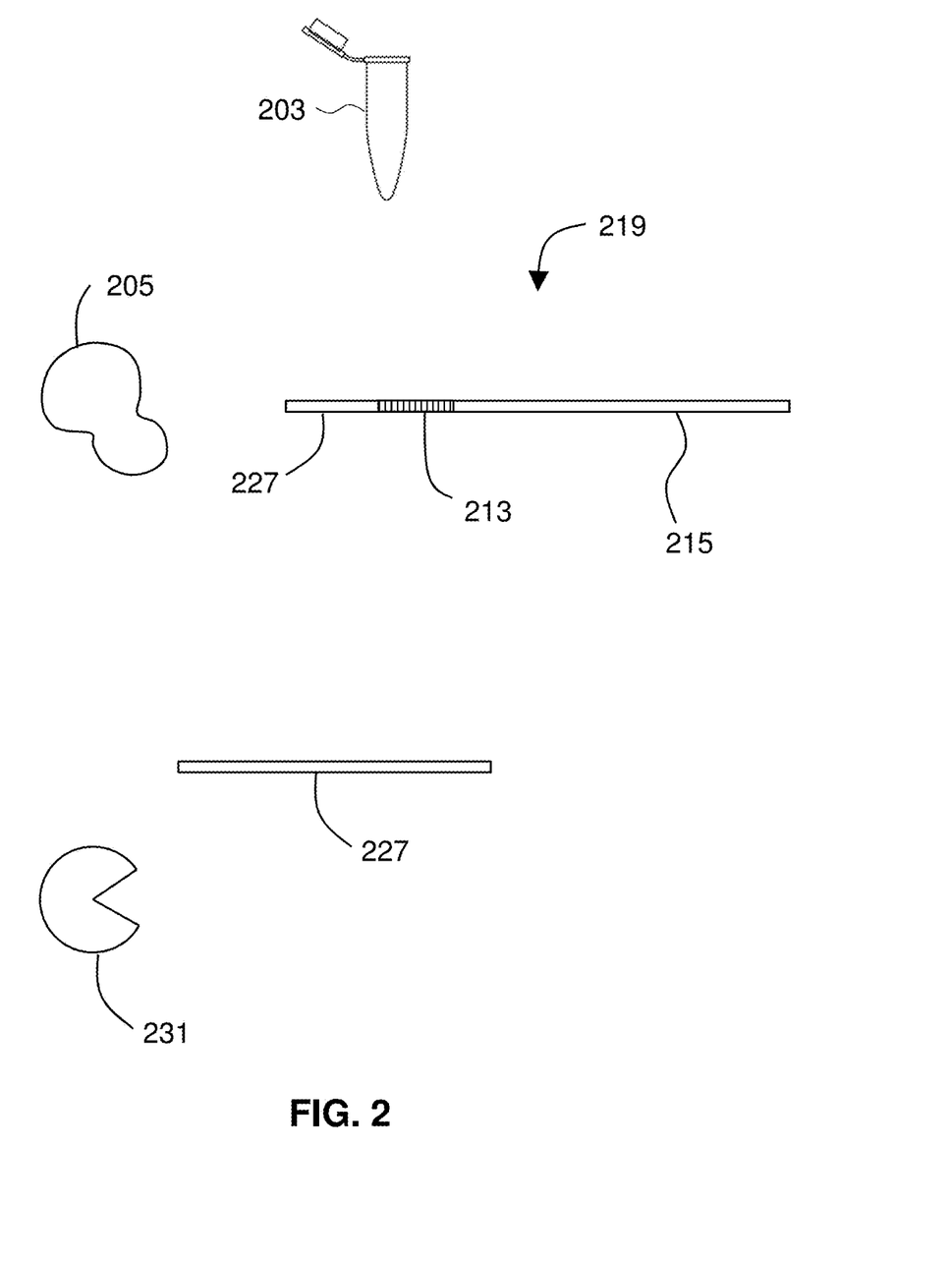
FIG. 2 depicts obtaining a sample according to certain embodiments.

FIG. 2 depicts obtaining a sample according to certain techniques. A biological or clinical representative sample 203 that contains tumor DNA 219 is obtained from a subject or patient. The depicted technique is useful for the isolation of, or enrichment for, a representative portion 215 of the tumor DNA. The technique may use any suitable sample 203. The enrichment technique includes obtaining a blood, plasma, or tissue sample from the patient. Preferably, the representative sample 203 includes tissue obtained by tumor biopsy. Optionally, a sample that includes plasma is obtained. In some embodiments, the representative sample 203 includes blood or plasma. In preferred embodiments, the representative sample 203 includes a tumor tissue sample (such as from a biopsy or a formalin-fixed, paraffin embedded tumor slice), or any other sample containing nucleic acid. In some embodiments, the representative portion comprises one or more DNA fragments at least a few kilobases in length. For example, the representative portion may be a long fragment (e.g., >8,000 bases) that includes portions of both genes and non-coding DNA, any or all of which may be sequenced.

Optionally, an enrichment is performed to obtain the representative portion from the tumor DNA. The enrichment may include selectively protecting the representative portion and degrading unprotected nucleic acid. Selectively protecting the representative portion may include introducing into the sample at least one molecule that selectively protects the representative portion from digestion in a sequence-specific manner (e.g., the at least one molecule is a guide RNA where selectively protecting the representative portion includes delivering the guide RNA and a Cas endonuclease to bind to, and protect, the representative portion in the sequence-specific manner, and degrading the unprotected nucleic acids includes digesting the unprotected nucleic acids with an exonuclease).

Optionally the representative portion does not include any portion of any oncogene. Embodiments of the method may include demonstrating that the representative portion is representative of the tumor DNA. In some embodiments, the demonstrating includes a genome-wide association study. In certain embodiments, methods for determining representativeness of the portion of tumor DNA include Bayesian methods for determining representativeness of a selection of loci. A Bayesian hierarchical model may be implemented to learn an informative prior distribution from sequence features. See Huang, 2017, BRIE: transcriptome-wide splicing quantification in single cells, Genome Biology 18(1):123, incorporated by reference. Bayesian Regression for Isoform Estimation (BRIE) is a statistical model that achieves extremely high sensitivity at low coverage by using informative priors learned directly from data via a (latent) regression model. The regression model couples the task of splicing quantification across different genes, allowing a statistical transfer of information from well-covered genes to less well covered genes, achieving considerable robustness to noise in low coverage. BRIE can be implemented to show that a portion of a target nucleic acid is representative of the target nucleic acid. BRIE can provide a reliable and reproducible method to quantify off-target active across genomes.

Embodiments of the invention include obtaining the representative portion by negative enrichment. Such enrichments may include protecting one or both ends of the representative portion then ablating or digesting any unprotected nucleic acid in the representative sample.

A molecule 205 or molecular complex is introduced to the sample, which molecule 205 will bind to a specific target 213. The binding target 213 is adjacent or overlaps representative portion 215 of tumor DNA. The representative portion 215 may be of any suitable length and the technique may be used to capture long DNA fragments, including individual fragments with lengths of thousands to tens of thousands of bases. The illustrated technique includes selectively protecting the representative portion 215 while degrading unprotected, non-target nucleic acids 227, thereby isolating the representative portion 215. Selectively protecting the fragment of DNA preferably includes using one or molecules 205 that interact with the representative portion 215 in a sequence-specific manner.

The molecules 205 or molecular complexes that interact with the fragment of DNA in a sequence-specific manner may include, for example, a DNA binding protein, an oligonucleotide, an endonuclease, a transcription-activator like effector (TALE) domain, a TALE nuclease (TALEN), a non-naturally occurring oligonucleotide (e.g., an oligo that includes a conformationally-restricted nucleotide or a phosphorothioate linkage), or any other sequence-specific binder. Thus preferably selectively protecting the at least one fragment includes introducing into the sample at least one molecule that selectively protects the target nucleic acid from digestion in a sequence-specific manner. In a preferred embodiment the molecule 205 or molecular complex includes a Cas endonuclease and a guide RNA that binds to the target 213.

Figure 3:
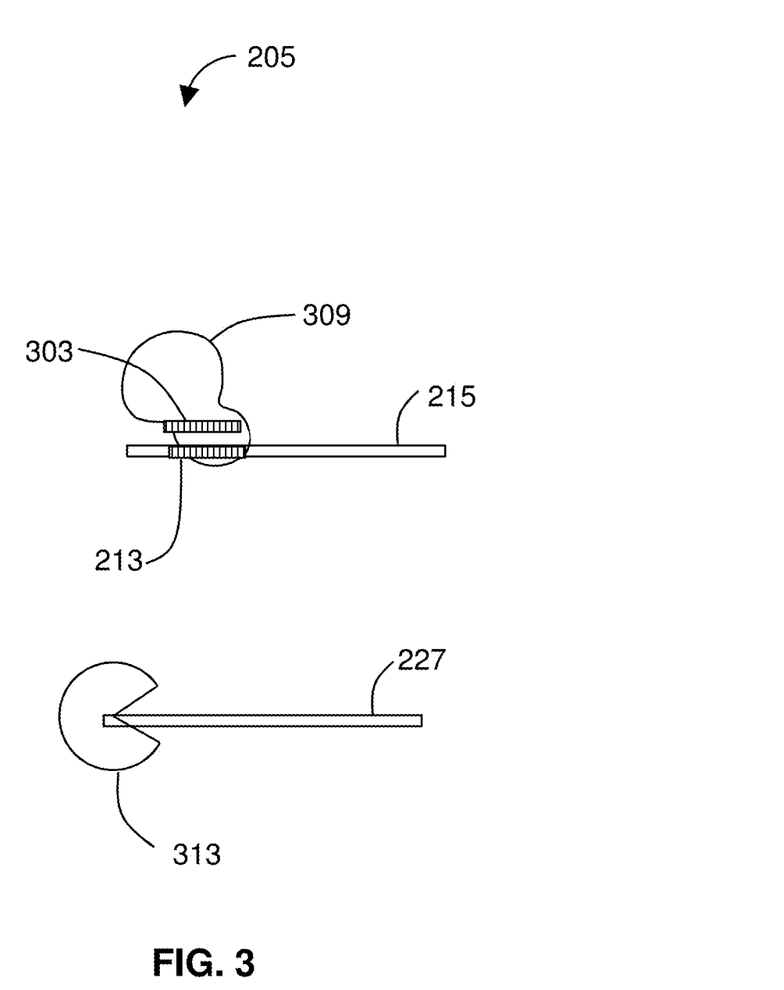
FIG. 3 shows Cas and guide RNA to protect target nucleic acid.

FIG. 3 shows delivering a guide RNA 303 and a Cas endonuclease 309 to bind to, and protect, the representative portion 215 in the sequence-specific manner. Because the guide RNA 303 complexes with the Cas endonuclease 309 and binds to the target 213 in a sequence-specific fashion, the depicted method may be used to selectively protect the representative portion 215. The method can be said to be selective in that one can select a representative portion 215 for enrichment and choose a proximal target 213. The guide RNA 303 and the Cas 309 selectively protect the selected representative portion 215. The non-target nucleic acids 227 can then be degraded. For example, the method may include digesting the non-target nucleic acids 227 with an exonuclease 313. Thus methods may include obtaining the representative portion 215 of the tumor DNA form the representative sample 203 by selectively protecting at least one fragment of the tumor DNA in a sequence-specific manner with a Cas endonuclease and a guide RNA and degrading unprotected nucleic acid, thereby isolating the representative portion of the tumor DNA, such that the at least one fragment is at least five thousand bases in length and is preferably about 10,000 bases in length.

A surprising feature is that catalytically inactive Cas (dCas) may be used, or active Cas may be used. Even when active Cas is used, it will bind to the representative portion 215 and successfully protect the representative portion 215 from the exonuclease 313 (preferably a dsDNA exonuclease).

In preferred embodiments, the enrichment technique is used to isolate long fragments for representative portion 215 of target tumor DNA. The depicted techniques will work to isolate or enrich for a fragment of the tumor DNA of at least a few kilobases in length. Preferred embodiments include capturing cell free DNA from the plasma sample and isolating fragments of tumor DNA. More preferably, the methods also include isolating fragments of matched normal DNA. Matched normal DNA may be taken to refer to DNA from non-tumorous cells of a patent ("normal"), where homologous segments of DNA from tumor cells ("matched") are also isolated. Methods are included for the sequence-specific isolation, or enrichment, of arbitrarily long DNA fragments, which methods due to the sequence specificity may have particular utility in enriching for both tumor DNA fragments and matched normal DNA fragments.

The method 101 may optionally include demonstrating that the representative portion 215 is representative of mutations in the tumor. For a portion of tumor DNA to be representative of mutations in the tumor may be understood to mean that a count of mutations in the sample (e.g., relative to a "matched normal" sample or a reference genome) can be reliably correlated to TMB for the tumor. In preferred embodiments, the representative portion is representative for TMB at two levels. At the first level, the representative sample 203 is representative of the tumor. At the second level, the portion of tumor DNA that is sequenced is representative of mutations in the tumor.

The first level carries the meaning that the tumor DNA may be less (e.g., fewer bases than) a whole exome or comprehensive oncogene panel but nevertheless the assayed tumor DNA provide information that can be reliably correlated to larger fraction of a tumor genome such as a whole exome or comprehensive oncogene panel. For example, the tumor DNA may be one or a few long fragments isolated by the technique described above. The second level carries the meaning that the sample is representative of the genetics (e.g., heterogeneity, clonality) of the tumor and takes into account heterogeneity, or clonality, that may be present within the tumor. In some embodiments, the sample is demonstrated to be representative of all nucleic acid of a tumor The sample may be demonstrated to be representative by any suitable method. Suitable methods may include whole genome sequencing, linkage analysis, comparative hybridization assays, or a genome-wide association study.

Some embodiments include whole genome sequencing of tumor nucleic acid. Tumor DNA is isolated and sequenced. The resultant sequence reads are assembled to reconstruct all or a substantial portion of a tumor genome. A number of mutations (relative to matched normal or a reference) for the whole tumor genome (i.e., ground truth TMB) is determined. Sample fractions of the tumor genome are also captured and sequenced, and mutation counts are obtained for those fraction. It will be expected that as the fraction of genome in the sample approaches 100% of the genome, an extrapolated mutation count for that fraction will approach ground truth TMB. It may be observed that the extrapolated mutation count approaches or stably converges on ground truth TMB at some fraction less than 100. In such cases, the stable convergence on ground truth demonstrates that the corresponding fraction is a representative sample. This whole genome sequencing (WGS) approach can be performed a limited number of times (e.g., once, or once per patient, or once per population, or once per polynucleotide enrichment technique), and then the sample that is thus shown to be representative can be used going forward. This approach may have applicability with a patient being treated for a tumor: e.g., the WGS is performed once at the beginning of treatment, and for subsequent monitoring or remission, only the representative sample is assayed.

Certain embodiments include a genome-wide association study (GWAS). A GWAS is a method of examining up to genome-wide sets of features associated with a trait. Here, a GWAS may be performed to determine an association between mutations at certain loci and TMB such that the representative portion of tumor DNA (e.g., the ≈10k length fragment isolated using Cas9) includes loci where mutations correlate with TMB.

Figure 4:
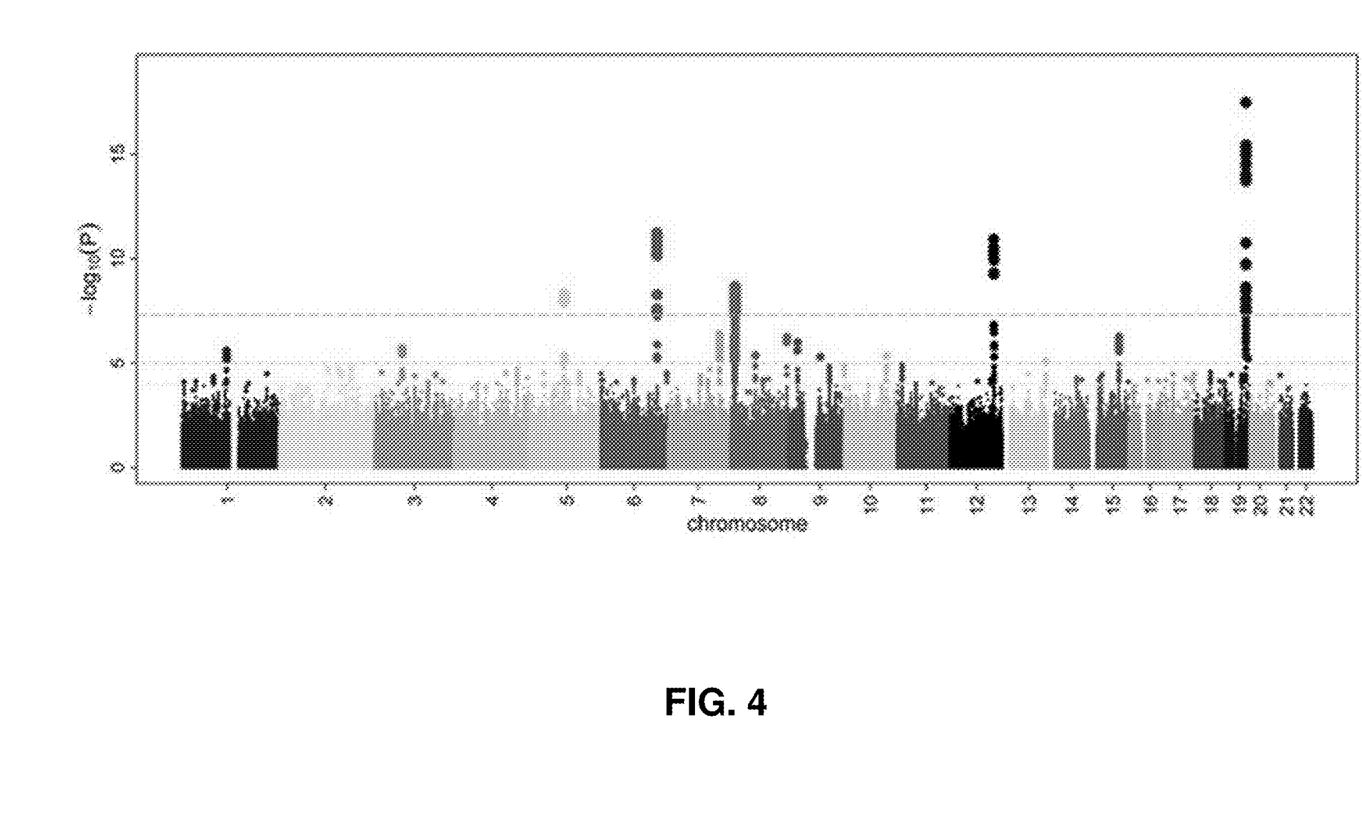
FIG. 4 gives exemplary results from a genome wide association study.

FIG. 4 shows results from a GWAS. In typical GWAS results, dots represent mutation with the y-axis showing association level. Genomic coordinates are displayed along the X-axis, and the negative logarithm of the association P-value for each mutation displayed on the Y-axis, such that each dot on the plot signifies a mutation. Because the strongest associations have the smallest P-values (e.g., 10-15), their negative logarithms will be the greatest. Thus where the studied, associated trait is TMB (e.g., as determined by WGS for a ground truth), points on the plot indicate genomic regions where mutations can be correlated to TMB.

Additionally, it may be beneficial to perform a GWAS with tumor and normal inputs. All loci are interrogated and, for each mutation, it is then determined if there are significant differences between tumor and normal inputs. A unit for reporting results may be an odds ratio. The odds ratio is the ratio of two odds, which in the context of GWA studies may include the odds of a mutation for tumor and for matched normal DNA. When a mutation is present in tumor DNA more frequently than in matched normal, the odds ratio is higher than 1. A P-value for the significance of the odds ratio is typically calculated using a simple chi-squared test. Finding odds ratios that are significantly different from 1 is the objective of the GWA to show that mutations at certain loci are associated with TMB.

A potential application of a GWAS is to demonstrate that a certain portion of tumor DNA serves as a representative portion for TMB in a manner that is uncoupled from a clinical assays. Thus if a patient has a genetic test performed, such as an assay for a panel of SNPs or sequencing of a small portion of certain genes, a GWAS that is independently performed may validate that the subject of the genetic test is usefully representative for TMB.

By demonstrating that a portion is representative for TMB, TMB may be determined by looking at loci that are surrogates for primary loci of interest. For example, where an established TMB tests involves sequencing at a plurality of genetic loci that includes exons of each of a plurality of genes (e.g., the genes are a "TMB panel"), method of the invention may be used to assay a representative sample that does not include any of the exons of the plurality of genes. To illustrate by example, an existing TMB test may include the complete sequencing of a panel of, e.g., >300 genes.

The following list illustrates an exemplary set of 321 genes that may be included in a TMB profile ("TMB Panel"): ABL1; BRAF; CHEK1; FANCC; GATA3; JAK2;

MITF; PDCD1LG2; RBM10; STAT4; ABL2; BRCA1; CHEK2; FANCD2; GATA4; JAK3; MLH1; PDGFRA; RET; STK11; ACVR1B; BRCA2; CIC; FANCE; GATA6; JUN; MPL; PDGFRB; RICTOR; SUFU; AKT1; BRD4; CREBBP; FANCF; GID4; KAT6A; ; MRE11A; PDK1; RNF43; SYK; AKT2; BRIP1; CRKL; FANCG; GLI1; KDM5A; MSH2; PIK3C2B; ROS1; TAF1; AKT3; BTG1; CRLF2; FANCL; GNA11; KDM5C; MSH6; PIK3CA; RPTOR; TBX3; ALK; BTK; CSF1R; FAS; GNA13; KDM6A; MTOR; PIK3CB; RUNX1; TERC; AMER1; CTCF; FAT1; GNAQ; KDR; MUTYH; PIK3CG; RUNX1T1; TERT; APC; CARD11; CTNNA1; FBXW7; GNAS; KEAP1; MYC; PIK3R1; SDHA; TET2; AR; CBFB; CTNNB1; FGF10; GPR124; KEL; MYCL; ; MYCL1; PIK3R2; SDHB; TGFBR2; ARAF; CBL; CUL3; FGF14; GRIN2A; KIT; MYCN; PLCG2; SDHC; TNFAIP3; ARFRP1; CCND1; CYLD; FGF19; GRM3; KLHL6; MYD88; PMS2; SDHD; TNFRSF14; ARID1A; CCND2; DAXX; FGF23; GSK3B; KMT2A; MLL; NF1; POLD1; SETD2; TOP1; ARID1B; CCND3; DDR2; FGF3; H3F3A; KMT2C; MLL3; NF2; POLE; SF3B1; TOP2A; ARID2; CCNE1; DICER1; FGF4; HGF; KMT2D; MLL2; NFE2L2; PPP2R1A; SLIT2; TP53; ASXL1; CD274; DNMT3A; FGF6; HNF1A; KRAS; NFKBIA; PRDM1; SMAD2; TSC1; ATM; CD79A; DOT1L; FGFR1; HRAS; LMO1; NKX2-1; PREX2; SMAD3; TSC2; ATR; CD79B; EGFR; FGFR2; HSD3B1; LRP1B; NOTCH1; PRKAR1A; SMAD4; TSHR; ATRX; CDC73; EP300; FGFR3; HSP90AA1; LY; N; NOTCH2; PRKCI; SMARCA4; U2AF1; AURKA; CDH1; EPHA3; FGFR4; IDH1; LZTR1; NOTCH3; PRKDC; SMARCB1; VEGFA; AURKB; CDK12; EPHA5; FH; IDH2; MAGI2; NPM1; PRSS8; SMO; VHL; AXIN1; CDK4; EPHA7; FLCN; IGF1R; MAP2K1; NRAS; PTCH1; SNCAIP; WISP3; AXL; CDK6; EPHB1; FLT1; IGF2; MAP2K2; NSD1; PTEN; SOCS1; WT1; BAP1; CDK8; ERBB2; FLT3; IKBKE; MAP2K4; NTRK1; PTPN11; SOX10; XPO1; BARD1; CDKN1A; ERBB3; FLT4; IKZF1; MAP3K1; NTRK2; QKI; SOX2; ZBTB2; BCL2; CDKN1B; ERBB4; FOXL2; IL7R; MCL1; NTRK3; RAC1; SOX9; ZNF217; BCL2L1; CDKN2A; ERG; FOXP1; INHBA; MDM2; NUP93; RAD50; SPEN; ZNF703; BCL2L2; CDKN2B; ERRFI1; FRS2; INPP4B; MDM4; PAK3; RAD51; SPOP; BCL6; CDKN2C; ESR1; FUBP1; IRF2; MED12; PALB2; RAF1; SPTA1; BCOR; CEBPA; EZH2; GABRA6; IRF4; MEF2B; PARK2; RANBP2; SRC; BCORL1; CHD2; FAM46C; GATA1; IRS2; MEN1; PAX5; RARA; STAG2; BLM; CHD4; FANCA; GATA2; JAK1; MET; PBRM1; RB1; and STAT3. In certain embodiments, the representative sample includes a few but not all, e.g., between 5 and 150, genes from that listed TMB Panel.

Using method of the invention, it may be demonstrated that fewer than the full list of 321 genes needs to be sequenced, mutations counted, and the mutation count extrapolated to show TMB. Moreover, it may be shown that a limited set of genes that do not appear in the TMB panel can be sequenced, and a mutation count can be reliably used as an input to determine TMB. For example, in some embodiments of the method 101, a sample comprising tumor DNA from a tumor in a patient is obtained, in which that sample includes a set of genes such as the following eleven genes ("Representative Panel"): HBA1; HBA2, HBB; FMR1; GBA; ASPA; MCOLN1; CFTR; SMPD1; DMD; and SMN1. In this example, the Representative Panel is a portion of tumor DNA representative of a plurality of genetic loci (e.g., the TMB panel), and mutations within the TMB panel are representative of a total number of mutations in the tumor. Importantly, methods of the invention may include determining or demonstrating (e.g., by WGS or GWAS) that the sample (e.g., the Representative Panel) is a representative of the plurality of genetic loci (e.g., the TMB panel).

Figure 5:
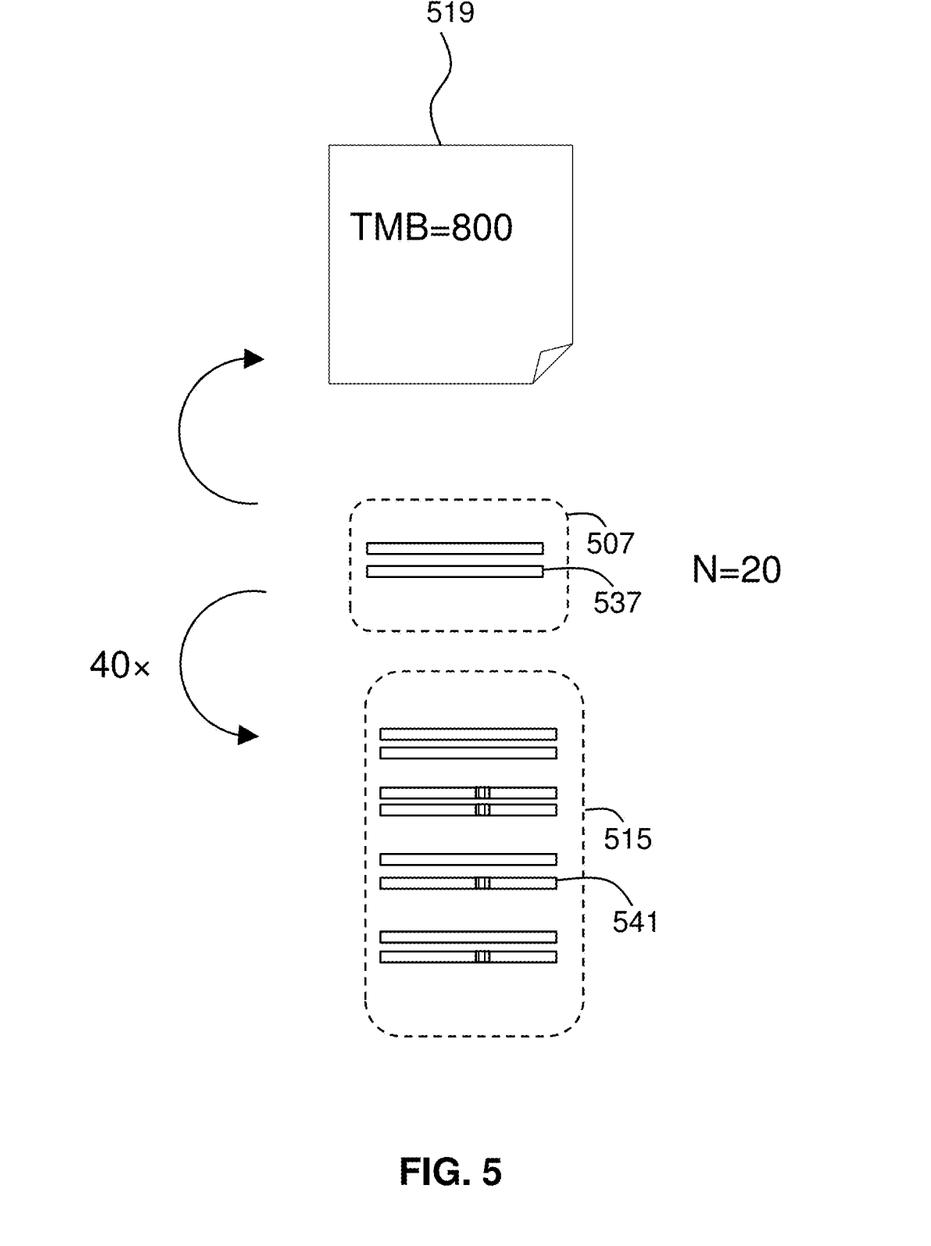
FIG. 5 shows determining TMB from a representative sample.

In some embodiments, the method address phenomena such as tumor heterogeneity to demonstrate that the plurality of genetic loci is representative of a total number of mutations in the tumor. For example, an expanded WGS assay may be formed to sequence the complete genomes of multiple cells from a tumor. Those complete genomes may be compared to a complete genome sequenced from the patient (e.g., the matched normal) and/or compared to a published reference genome and/or a cancer mutation database. Those comparisons may yield a complete count of mutations from the genome, TMB (e.g., a TMB that is more accurate and informative than obtained by simply sequencing a TMB panel). For a given tumor type, cancer stage, patient, or population, a relationship between true TMB and TMB from a TMB Panel may be determined to show that true TMB can reliably be determined by sequencing the representative sample. Determining that TMB from sequences from the representative sample may include extrapolating the TMB from a count of the determined differences. It may be found that the relationship between TMB and the count of determined difference is not linear, but curve-fitting techniques may be employed to show how TMB can be reliably predicted from a quantity of input sample. Thus the invention includes methods that include obtaining a sample demonstrably representative of a fraction of tumor nucleic acid that is demonstrably representative of genotype of a tumor FIG. 5 illustrates the principle by which TMB is determined from a representative sample. Here, a representative portion 507 of tumor DNA 537 is sequenced. The representative portion 507 is a subset of a complete TMB panel 515 of the tumor DNA 541 (e.g., TMB pane 515 includes about three hundred whole genes). However, a quantity of tumor DNA 537 in the representative portion 507 has been determined (e.g., the tumor DNA 537 is any arbitrary 2.5% of the TMB panel 515) at which true TMB extrapolates linearly or predictably from a count of mutations in the representative portion 507. A count (n=20) of mutations in the representative sample is determined. Because the TMB panel 515 includes 40× the quantity of DNA compared to the representative portion 507, a report 519 is provided in which TMB is shown as 800 (i.e., N=20×40). Here, TMB predictably correlates with the count of determined differences. Thus it can be shown that the portion 507 is representative of a total number of mutations in the tumor. Because the portion is representative of a total number of mutations in the tumor, the TMB predictably correlates with the determined differences.

From such principles, it may be understood that the assayed tumor DNA need not be a panel of cancer-associated genes. For example, in some embodiments, the tumor DNA comprises one or more housekeeping genes. It may be found that a count of mutations in a set of housekeeping genes—such as genes for transcription factors, RNA splicing proteins, translation factors, ribosomal proteins, mitochondrial ribosomal proteins, RNA polymerase, heat shock proteins, histones, cell-cycle proteins, apoptosis genes, oncogenes, DNA repair and replication genes, metabolic genes, NADH dehydrogenase, cytochrome c oxidase, ATPase, lysosome, proteasome, ribonuclease, cytoskeletal genes, cell adhesion proteins, or other such genes—predictably relate to TMB. It may also be understood that the tumor DNA that gets assayed may be a smaller sample than is assayed in a comprehensive genome profile of tumor-associated genes. In preferred embodiments, the tumor DNA that is sequenced includes fewer than one million bases of DNA.

Figure 6:
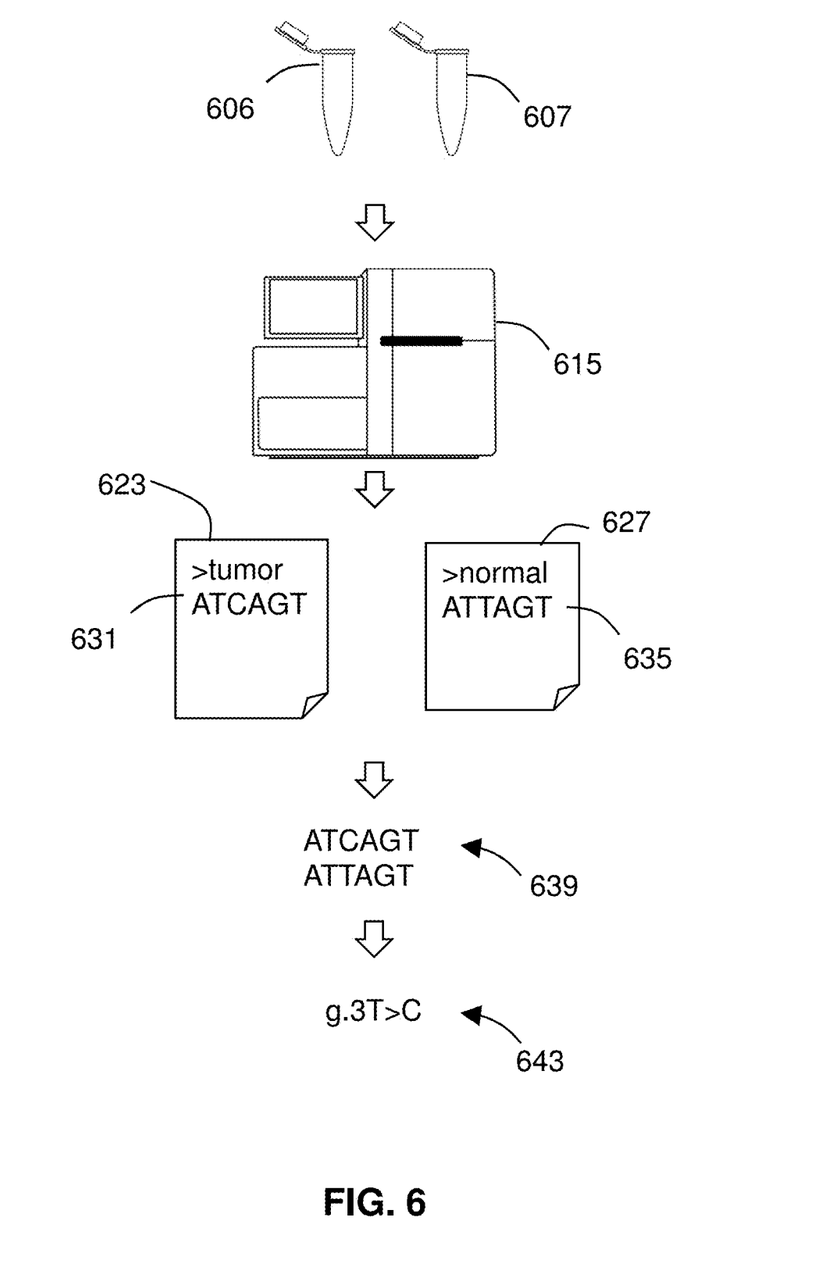
FIG. 6 illustrates methods of the invention.

FIG. 6 shows systems and reagents useful for performing methods of the invention, and shows how methods of the invention are performed. In certain embodiments, a sample 606 comprising tumor DNA is obtained from a tumor in a patient. Additionally, a matched normal sample 608 is obtained. In preferred embodiments, the sample 606 includes tissue from a tumor or plasma comprising cell-free DNA from the patient, such that the tumor DNA is circulating tumor DNA from the sample. A representative portion of the sample 606 and a corresponding matched normal portion 608 may be sequenced using a suitable sequencing instrument 615. Sequencing the tumor DNA and matched normal produces sequence reads. In some embodiments, identifying the mutations includes determining differences between the portion of the tumor DNA and matched normal DNA. In some embodiments, determining differences between the portion of the tumor DNA and the matched normal DNA comprises: sequencing the portion of the tumor DNA and the matched normal DNA to produce tumor sequences and normal sequences; and aligning the tumor sequences to the normal sequences. The method may include aligning the tumor sequences or the normal sequences to a reference genome, and further wherein the determine differences include bases and small indels in the tumor DNA that are unmatched at homologous portions of the normal DNA and the reference genome.

In preferred embodiments, obtaining the representative portion of the sample 606 includes selectively protecting at least one fragment of the tumor DNA in a sequence-specific manner with a Cas endonuclease and a guide RNA and degrading unprotected, non-target nucleic acids, thereby isolating the tumor DNA. In some embodiments, the polynucleotide enrichment is performed to isolate long fragment(s) of DNA such that the at least one fragment is, for example, at least five thousand bases in length. Preferably, the representative portion of the tumor DNA is one or more isolated fragments of several thousand bases (e.g., 10,000) in length. In some embodiments, the representative portion of the tumor DNA includes one or more housekeeping genes. In some embodiments, the portion of tumor DNA includes fewer than one million bases of DNA.

Sequence reads may be provided in any suitable format such as *.bcl, FASTA, or FASTQ files 223, 227. Preferably a tumor sequence file 223 includes a tumor sequence read 631, while a matched normal sequence file 635 contains a matched normal sequence read 635. Alternatively or additionally, the sequence reads may be assembled, e.g., by de novo assembly or by mapping to a reference. The result of an assembly may be a contig or consensus sequence that is analyzed in downstream steps of the method. Whether contigs, consensus sequences, or sequence reads, the method includes determining differences between the tumor DNA and the matched normal DNA. The differences may be determined by performing an alignment 639 between the a tumor sequence read 631 and the matched normal sequence read 635. Optionally, the method may include aligning the tumor sequences or the normal sequences to a reference genome.

Thus the method includes aligning the tumor sequences to the normal sequences. Differences (e.g., mutations, variants, variations) are called (which may be reported as one or more variants 643) and may be put into a report or stored so that a count of differences can be made. Preferably, the determine differences include bases and small indels in the tumor DNA that are unmatched at homologous portions of the normal DNA and the reference genome. The method includes reporting tumor mutation burden (TMB) based on the determined differences.

Thus methods of the invention include obtaining tumor DNA from a tumor of patient, in which the obtained tumor DNA does not include a plurality of known oncogenes. A number of mutations in the tumor DNA is identified and the methods include determining, from the number of mutations, tumor mutation burden for the tumor based on a relationship by which the tumor DNA is representative of a genome of the tumor. The sample, preferably, is sample demonstrably representative of a tumor and the sequenced portion is preferably demonstrably representative of mutations in a tumor. In a most preferred embodiment, the representative portion is obtained in a locus-agnostic fashion. I.e., the fragment enrichment process is designed to select fragments for ease or reproducibility, but without regard to, or knowledge of, specific known cancer genes or tumor biomarkers. The representative portion is captured in a locus-agnostic manner. Mutations in the representative portion are identified or counted. The method may include showing that the TMB predictably correlates with the identified mutations, thereby showing that the representative portion is representative of mutations in the tumor and that the representative By potentially independently showing the portion of tumor DNA to be representative, it is not required to capture and sequence a particular pre-defined set of loci, such as a TMB panel or comprehensive genomic profile of a plurality of genes. Instead, the sample capture can proceed by methods or techniques (such as polynucleotide enrichment by sequence-specific protections using entities such as Cas endonucleases and guide RNAs) that can be designed for optimal function (e.g., long-fragment (>5 kb) enrichment) without regard to the loci in the sample. As long as the sample is a representative sample, as may be independently demonstrated, the sample may be used for prediction of TMB.

In preferred embodiments, the sample includes a portion of tumor DNA, i.e., fragments of nucleic acid from one or more genomes of cancerous cells in a tumor in a patient. Any suitable tumor may be assayed, such as a tumor associated with breast cancer, lung cancer, colorectal cancer, cervical cancer, etc. The tumor DNA is obtained from a patient, who may be a person present in a clinical setting for diagnosis or treatment, or the patient may be a person from whom a tumor sample is possessed and known to be associated with that person (e.g., a formalin-fixed, paraffin embedded (FFPE) tumor slice from a known person). The sample includes the tumor DNA and may be any suitable sample, such as blood, plasma, other bodily fluid or tissue. Blood, plasma, or bodily fluid may be provided in a suitable container such as a blood collection tube such that sold under the trademark VACUTAINER by BD (Franklin Lakes, N.J.). Blood, plasma, or other bodily fluid or tissue may be in other formats such as slide mounted (e.g., FFPE tissue sections).

Figure 7:
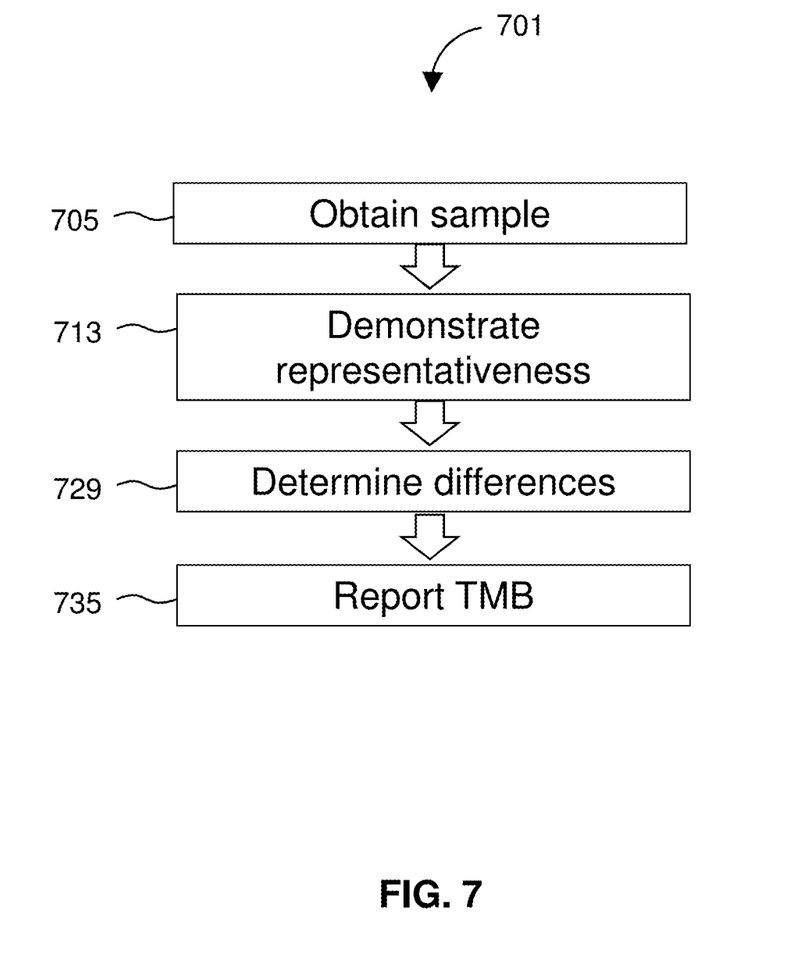
FIG. 7 diagrams exemplary embodiments of methods of the invention.

Aspects of the invention provide a method 701 of analyzing a tumor.

FIG. 7 diagrams the method 701. The method 701 may include obtaining a sample comprising tumor DNA from a patient. The method 701 includes demonstrating that a region of the tumor DNA is a representative sample for tumor mutation burden (TMB) (e.g., by whole genome sequences or a genome wide association study, or any other suitable means). The method 701 includes determining differences between the tumor DNA and matched normal DNA and reporting TMB based on the determined differences. The differences may be determined by comparing the region to a homologous region of non-tumor nucleic acid from the patient (e.g., to "matched normal" DNA). The comparison may be done by sequencing tumor DNA and matched normal DNA, or the comparison may be done by any other suitable method include, for example, comparative genomic hybridization assays, assaying for SNPs with a SNP chip, allele-specific primers used in an amplification or ligation assay, or other such methods. Embodiments include a method that includes obtaining a portion of tumor DNA demonstrably representative of mutations in a tumor from a sample that is demonstrably representative of a tumor. Because the sample is representative, it may be locus-agnostic. Thus in some embodiments of the method 701, obtaining the sample includes selectively protecting at least one fragment of the tumor DNA in a sequence-specific manner with a Cas endonuclease and a guide RNA and degrading unprotected, non-target nucleic acids, thereby isolating the tumor DNA. Preferably, the resultant isolated fragment is at least 5,000 bases in length.

Embodiments include a method of analyzing a tumor by obtaining tumor DNA from a tumor of patient, wherein the obtained tumor DNA does not include a plurality of known oncogenes; identifying a number of mutations in the tumor DNA; and determining—from the number of mutations—tumor mutation burden for the tumor based on a relationship by which the tumor DNA is representative of a genome of the tumor.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of analyzing a tumor, the method comprising:
   obtaining a representative sample of a tumor, the sample comprising tumor DNA;
   performing an enrichment of a target nucleic acid in the representative sample by introducing a Cas endonuclease and associated guide RNA to bind and protect the target nucleic acid in the tumor DNA that is representative of mutations in the tumor in a sequence-specific manner, and degrading unprotected nucleic acids with an exonuclease;
   sequencing the target nucleic acid to identify mutations;
   associating the identified mutations with a tumor mutation burden (TMB) of the tumor; and
   reporting the TMB based on the identified mutations.

2. The method of claim 1, wherein the representative sample comprises tissue obtained by tumor biopsy.

3. The method of claim 1, further comprising isolating the target nucleic acid from the representative sample without targeting known, specified tumor biomarkers.

4. The method of claim 1, wherein the target nucleic acid comprises one or more DNA fragments at least a few kilobases in length.

5. The method of claim 1, further comprising demonstrating that the target nucleic acid is representative of the tumor DNA.

6. The method of claim 5, wherein the demonstrating includes a genome-wide association study.

7. The method of claim 1, wherein the target nucleic acid does not include any portion of any oncogene.

8. The method of claim 1, wherein identifying the mutations includes determining differences between the target nucleic acid and matched normal DNA.

9. The method of claim 8, wherein determining differences between the target nucleic acid and the matched normal DNA comprises:
   sequencing the target nucleic acid and the matched normal DNA to produce tumor sequences and normal sequences; and
   aligning the tumor sequences to the normal sequences.

10. The method of claim 9, further comprising aligning the tumor sequences or the normal sequences to a reference genome, and further wherein the differences include bases and small indels in the tumor DNA that are unmatched at homologous portions of the normal DNA and the reference genome.

11. The method of claim 1, wherein the tumor DNA comprises one or more housekeeping genes.

12. The method of claim 1, wherein the target nucleic acid comprises fewer than one million bases of DNA.

13. The method of claim 1, wherein the representative sample comprises plasma comprising cell-free DNA from the patient, and wherein the tumor DNA is circulating tumor DNA from the sample.

* * * * *